United States Patent [19]

Nestor, Jr. et al.

[11] Patent Number: 4,690,916

[45] Date of Patent: Sep. 1, 1987

[54] NONA AND DECAPEPTIDE ANALOGS OF LHRH USEFUL AS LHRH ANTAGONISTS

[75] Inventors: John J. Nestor, Jr., San Jose; Brian Vickery, Cupertino, both of Calif.

[73] Assignee: Syntex (U.S.A.) Inc., Palo Alto, Calif.

[21] Appl. No.: 671,153

[22] Filed: Nov. 13, 1984

[51] Int. Cl.[4] .................. A61K 37/43; C07K 7/20
[52] U.S. Cl. .................................... 514/15; 514/800; 530/313
[58] Field of Search ............ 260/112.5 LH; 530/313, 530/328; 514/15, 800

[56] References Cited

U.S. PATENT DOCUMENTS 4,481,190  11/1984  Nestor et al. ............ 260/112.5 LH
4,530,920   7/1985  Nestor et al. ............ 260/112.5 LH
4,581,169   4/1986  Nestor et al. ................. 530/328

OTHER PUBLICATIONS

Phelps et al., *Endocrinology*, 100, 1526–1532 (1977).

Primary Examiner—Delbert R. Phillips
Attorney, Agent, or Firm—Liza K. Toth; Tom M. Moran

[57] ABSTRACT

Synthetic nonapeptide and decapeptide LHRH antagonist analogues having a halo lower alkyl guanadino-substituted amino acyl residue at position six are disclosed herein.

13 Claims, No Drawings

NONA AND DECAPEPTIDE ANALOGS OF LHRH USEFUL AS LHRH ANTAGONISTS

BACKGROUND OF THE INVENTION

Luteinizing hormone (LH) and follicular stimulating hormone (FSH) are released from the anterior pituitary gland under the control of the releasing hormone LHRH produced in the hypothalamic region. LH and FSH act on the gonads to stimulate the synthesis of steroid hormones and to stimulate gamete maturation. The pulsatile release of LHRH, and thereby the release of LH and FSH, controls the reproductive cycle in domestic animals and humans.

LHRH also affects the placenta, and the gonads indirectly, in causing the release of chorionic gonadotropin (hCG).

Antagonists of LHRH are useful for the control of fertility. Such antagonists block ovulation in the female and suppress spermatogenesis in the male. Related to these effects is a suppression of normal circulating levels of sexual steroids of gonadal origin, resulting in reduction in accessory organ weight and function in the male and the female. In domestic animals this effect promotes weight gain in a feed-lot situation, stimulates abortion in pregnant animals and in general, acts as a chemical sterilant.

The natural releasing hormone LHRH is a decapeptide comprised of naturally occuring amino acids (which have the L-configuration except for the achiral amino acid glycine). Its sequence is as follows:

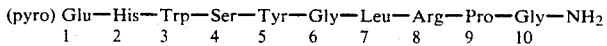

Many analogs of this natural material have been studied and the very large majority of them have proven to be of insufficient biological activity to be clinically useful. Certain select modifications have proven to have an agonist effect on biological activity. By far the most significant enhancement is obtained by changing the 6-position residue from Gly to a D-amino acid.

In addition to agonists, analogs have been prepared which are competitive antagonists to LHRH; all of which require deletion or replacement of the histidine residue at position 2; Vale, W., et al, *Science,* 176: 933 (1972). In general, it appears that a D-amino acid placed in the sequence at that position gives the best activity; Rees, R. W. A., et al, *J. Med. Chem.* 17: 1016 (1974).

It has also been shown that adding a modification at the 6 position, which, without the modification at position 2, results in the agonist activity cited above, enhances the antagonist activity of the 2-modified analogs; Beattie, C. W., et al, *J. Med. Chem.,* 18: 1247 (1975); Rivier, J., et al, *Peptides* 1976 p. 427, Editions de l'Universite de Bruxelles, Belgium (1976).

Against the background of these two major alterations, which result in a potent series of LHRH antagonists, additional increments in antagonist activity may be had by modifying positions 1, 3 and/or 10 in the already 2, 6 modified peptide. Coy, D. H., et al *Peptides* 1976, p. 462, Editions de l'Universite de Bruxelles, Belgium (1976); Rivier, J. E., et al, *Life Sci.* 23: 869 (1978); Dutta, A. S., et al, *Biochem Biophys. Res. Commun.* 81: 382 (1978), Humphries, J., et al, *Biochem. Biophys. Res. Commun.,* 85: 709 (1978). It has also been shown that N-acylation of the amino acid at position 1 is helpful; Channabasavaia, K., et al, *Biochem. Biophys. Res. Commun.* 81: 382 (1978); Coy, D. H., et al, *Peptides.—Structure and Biological Function* p. 775, Pierce Chemical Co. (1979). Additionally, (N-Ac-D-p-Cl-Phe[1], D-p-Cl-Phe[2], D-Trp[3], D-Arg[6], D-Ala[10])LHRH has been published by D. H. Coy, Endocrinology, 110, 1445 (1982). In another instance D-Ala[4] modification to LHRH has been reported to retain antagonist activity. See E. Pedroza, J. A. Martinez, D. H. Coy, A. Arimura and A. V. Schally; Int. J. Fert.; 23, 294 (1978).

Since antagonists function by competing with LHRH for the appropriate receptors, high dosages of these compounds are required in order to block out the natural peptide. It is especially desirable, in view of this, to obtain antagonists with a very high degree of potency and prolonged activity. The ability to be slowly released from depot formulations will also be important. The analogs known till now require comparatively high levels of compound, with the attendant problems of increased possibility for toxicity and other side effects.

SUMMARY OF THE INVENTION

The present invention refers to novel, highly potent nonapeptide and decapeptide analogs of LHRH in which a replacement at position 2, (thus converting the peptide to the antagonist series) is made more effective by replacement of the glycine residue at position 6 by a novel halo lower alkyl guanido-substituted amino acid residue which does not occur in nature. These compounds are several times more potent than any other presently known N,N'-disubustituted guanidino containing LHRH antagonists. Further enhancements by substitutions at 1, 2, 3, 4, 7 and/or 10 are also disclosed. The invention is also directed to various methods of use of these compounds and to pharmaceutical compositions therefor. A further aspect of the invention involves processes for the preparation of the novel compounds described above.

DETAILED DESCRIPTION OF THE INVENTION

Description of the Analogs

The present invention relates to novel nonapeptide and decapeptide analogs of LHRH which have the formula

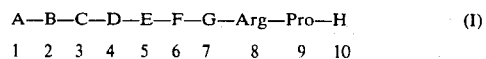

and the pharmaceutically acceptable salts thereof, wherein:

A is an amino acyl residue selected from the group consisting of N-Ac-D,L-$\Delta^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threnoyl, N-Ac-D,L-alanyl, N-Ac-3-(1-naphthyl)-D,L-alanyl, N-Ac-3-(2-naphthyl)-D,L-alanyl, N-Ac-3-(2,4,6-trimethylphenyl)-D,L-alanyl, and N-Ac-3-(4-trifluoromethylphenyl)-D,L-alanyl;

B is an amino acyl residue selected from the group consisting of D-phenylalanyl, D-p-Cl-phenylalanyl, D-p-Br-phenylalanyl, D-p-F-phenylalanyl, D-p-nitrophenylalanyl, 3-(3,4,5-trimethoxyphenyl)-D-alanyl, 2,2- diphenylglycine, D-α-methyl-p-Cl-phenylalanine and 3-(2,4,6-trimethylphenyl)-D-alanyl;

C is an amino acyl residue selected from the group consisting of D-tryptophanyl, D-phenylalanyl, D-Me$_5$-phenylalanyl, 3-(3-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl residue selected from the group consisting of the radicals represented by the following structural formulas:

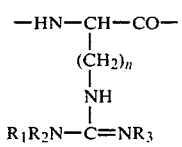 (II)

wherein
n is 1 to 5;
R$_1$ is halo lower alkyl;
R$_2$ is hydrogen, methyl or ethyl;
R$_3$ is R$_1$, methyl, ethyl or —CH$_2$CH$_2$OH;
G is an amino acyl residue selected from the group consisting of L-tryptophanyl, L-Nal(2), L-leucyl, L-norleucyl and L-norvalyl;
H is D-alaniamide, D-leucinamide, glycinamide or —NHR$_5$ wherein R$_5$ is lower alkyl or NHCONH$_2$; and the pharmaceutically acceptable salts thereof.

The replacement of the L-histidyl residue which is at position 2 in LHRH with one of the residues herein specified is a requirement to convert the peptide to an LHRH antagonist. The replacement of the glycyl residue at position 6 in LHRH with one of the residues specified as F gives a dramatic enhancement of the antagonist effect. The substitutions disclosed herein at positions 1, 2, 3, 4, 7 and 10 are further helpful in enhancing the antagonist activity.

Abbreviations and Definitions

As set forth above, and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972). These represent L-amino acids, with the exception of the achiral amino acid glycine, and with the further exception of any unnatural or natural amino acids which are achiral, or are otherwise designated as D-. All peptide sequences mentioned herein are written according to the generally accepted convention whereby the N-terminal amino acid is on the left and the C-terminal amino acid is on the right.

Certain other abbreviations will be useful in describing the invention. The present invention employs replacements by amino acids which do not occur in nature. Particularly commonly employed among these are the following:

| Amino acid residue | Abbreviation |
| --- | --- |
| 3-(2-naphthyl)-D-alanyl | D-Nal(2) |
| 3-(p-fluorophenyl)-D-alanyl | D-p-F—Phe |
| 3-(p-chlorophenyl)-D-alanyl | D-p-Cl—Phe |
| 3-(p-bromophenyl)-D-alanyl | D-p-Br—Phe |
| 3-(2,3,4,5,6-pentamethylphenyl)-D-alanyl | D-Me$_5$Phe |
| 3-(2,4,6-trimethylphenyl)-D-alanyl | D-Tmp |
| 3-(3,4,5-trimethoxyphenyl)-D-alanyl | D-Tmo |
| 3-(4-(trifluoromethylphenyl)-D-alanyl | D-Ptf |
| N$^G$,N$^{G'}$-bis(2,2,2-trifluoroethyl)-D-homoarginine | D-FDeh |
| N$^G$-methyl,N$^{G'}$-(2,2,3,3,3-pentafluoropropyl)-D-homoarginine | D-mfPh |

As a further convenience, since the amino acid sequence of LHRH has been shown to be

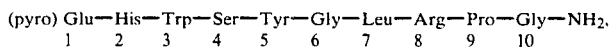

nona- and decapeptides in which the amino acid residues at particular places in the sequence have been replaced by other amino acid residues or other moieties are abbreviated by showing the nature of the substitution, superscribed by the location, followed by LHRH as the parent.

Thus, for example, the sequence,

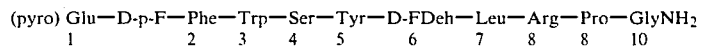

in which the Gly at position 6 has been replaced by D-FDeh and the His at position 2 has been replaced by D-p-Fe-Phe, is represented [D-p-F-Phe$^2$, D-FDeh$^6$]LHRH; and the sequence

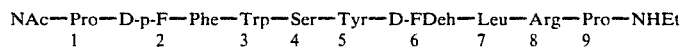

is represented: [NAc-Pro$^1$, D-p-F-Phe$^2$, D-FDeh$^6$, Pro$^9$-NHEt]LHRH.

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or (c) combinations, of (a) and (b), e.g., a zinc tannate salt and the like.

"Halo lower alkyl" refers to a lower alkyl radical substituted with halo groups, especially those having one, two or three halo groups on the ω-carbon. The halo group may be fluoro, chloro or bromo. This group is exemplified by trifluoromethyl, 2,2,2-trifluoroethyl, 3,3,3-trifluoropropyl, 2,2,2-trichloroethyl and the like.

For the purpose of this invention the abbreviation "alkylPro" refers to cis-5-alkyl-L-prolyl residue wherein alkyl is the same as "lower alkyl" defined above. More specifically "MePro" is cis-5-methyl-L-Prolyl, "EtPro" is cis-5-ethyl-L-Prolyl and "ButPro" is cis-5-n-butyl-L-Prolyl.

The abbreviation "N-Ac" refers specifically to the N-acetyl amino acid residue in conformance with generally accepted nomenclature.

PREFERRED EMBODIMENTS OF THE COMPOUNDS

Compounds which are preferred embodiments of the present invention are those wherein A is N-Ac-L-Pro, N-Ac-D-Ser, N-Ac-D-p-Cl-Phe, N-Ac-D-Nal(2); B is D-p-F-Phe or D-p-Cl-Phe; C is D-Trp, D-Nal(2) or D-Phe; D is Ser; E is Tyr; F is the compound of Formula II wherein n is 3 or 4, and halo lower alkyl is trifluoromethyl, 2,2,2-trifluoroethyl, 3,3,3-trifluoropropyl, 2,2,3,3,3-pentafluoropropyl, or 3,3,3-trichloropropyl.

More preferred embodiments herein are:
A is N-Ac-D-Nal(2) or N-Ac-D-p-Cl-Phe, B is D-p-F-Phe or D-p-Cl-Phe, C is D-Nal(2), or D-Trp, D is Ser, E is Tyr, F is D-FDeh and H is D-AlaNH$_2$, GlyNH$_2$ or NHEt;

Most preferred are the compounds
N-Ac-D-Nal(2)-D-pCl-Phe-D-Trp-Ser-Tyr-D-FDeh-Leu-Arg-Pro-D-AlaNH$_2$,
N-Ac-D-Nal(2)-D-p-Cl-Phe-D-Trp-Ser-Tyr-D-FDeh-Trp-Arg-Pro-D-AlaNH$_2$,
N-Ac-D-Nal(2)-D-p-Cl-Phe-D-Trp-Ser-Tyr-D-FDeh-Nal(2)-Arg-Pro-D-AlaNH$_2$, and
N-Ac-D-Nal(2)-D-p-Cl-Phe-D-Trp-Ser-Tyr-D-mfph-Nal(2)-Arg-Pro-D-AlaNH$_2$.

Assay Procedures

The compounds of this invention and, particularly, the salts thereof, exhibit surprisingly potent and long lasting LHRH antagonist activity.

Primary measures of potency are ability to inhibit ovulation in rats, as assayed by the procedure of Corbin, A. and Beattie, C. W., *Endocrine Res. Commun.*, 2: 1 (1975) and ability to inhibit LH release and ovulation in the rabbit, as per Phelps, C. P., et al, *Endocrinology* 100: 1526 (1977).

Other bioassays which are used for LHRH antagonists and for the compounds of the present invention are:

(a) inhibition of LHRH induced FSH and LH release in the rat, in vivo; Vilchez-Martinez, J. A., et al, *Endocrinology*, 96: 1130 (1975); and, (b) inhibition of LH and FSH release by dispersed anterior pituitary cell cultures as measured by radioimmuno assay. (Vale, W., et al, *Endocrinology* 91: 562 (1972).

Antagonist Effects and Utilities

The following utilities flow from the antagonist effect of the compounds herein:

female contraception;
ovulation suppression or delay;
induction of parturition;
synchronization of ovulation;
estrus suppression;
growth promotion in female animals;
luteolysis, menses induction;
early, first trimester abortifacient;
therapy for endometriosis;
therapy for mammary and cysts
therapy for polycystic ovary syndrome (Stein-Leventhal);
therapy for benign prostatic hypertrophy;
male contraception;
gonadal protection during cancer therapy;
therapy for diseases which result from excessive gonadal hormone production in either sex;
pregnancy termination in pets;
functional castration in male food producing animals;
suppression of proestrous bloody discharge in dogs;
suppression of menopausal symptoms.

The aspect of the present invention which relates to particular uses for the above-described compounds is concerned with these utilities, most particularly inhibition of ovulation and treatment of endometriosis in the female, and inhibition of spermatogenesis and treatment of prostatic tumors in the male.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally buccally (including sublingually), transdermally or intranasally. The most suitable route in any given case will depend upon the use, particular active ingredient, the subject involved, and the judgement of the medical practitioner. The compound or composition may also be administered by means of slow-release, depot or implant formulations as described more fully herein below.

In general for the uses herein above described, it is expedient to administer the active ingredient in amounts between about 0.01 and 10 mg/kg body weight per day, preferably between about 0.01 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in *Remington's Pharmaceutical Sciences,* Mack Publishing Company, Easton, PA., 1970. Formulations for parenteral administration may contain as common excipients sterile water or saline, polyalkylene glycols such as polyethylene glycol, oils of vegetable origin, hydrogenated napthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example (a) an acid addition salt with a polybasic acid such as phosphoric acid, sulfuric acid, citric acid, tartaric acid, tannic acid, pamoic acid, alginic acid, polyglutamic acid, napthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix pellets, particularly for use in animals. Additional slow release, depot or implant formulations, e.g. liposomes, are well known in the literature. See, for example, *Sustained and Controlled Release Drug Delivery Systems,* J. R. Robinson ed., Marcel Dekker, Inc., New York, 1978. Particular reference with respect to LHRH type compounds may be found, for example, in U.S. Pat. No. 4,010,125.

Synthesis of the Peptides

The polypeptides of the present invention may be synthesized by any techniques that are known to those skilled in the peptide art. An excellent summary of the many techniques so available may be found in J. M. Stewart and J. D. Young, *Solid Phase Peptide Synthesis,* W. H. Freeman Co., San Francisco, 1969, and J. Meienhofer, *Hormonal Proteins and Peptides,* Vol. 2, p. 46., Academic Press (New York), 1973 for solid phase peptide synthesis and E. Schroder and K. Lubke, *The Peptides,* Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) and removed seqentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Preferred Embodiments of Synthesis

A particularly preferred method of preparing compounds of the present invention involves solid phase peptide synthesis.

In this particularly preferred method the α-amino function of the amino acids is protected by an acid or base sensitive group while the side chain functional groups may be free or protected. Such protecting groups for the α-amino function should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, 1,1-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; or the juanidino function may be unprotected and incorporated as Boc-Arg-OH (the tetraphenylborate -salt); for tyrosine:benzyl, o-bromobenzyloxycarbonyl, 2,6-dichlorobenzyl, isopropyl, cyclohexyl, cyclopentyl and acetyl; for serine:benzyl and tetrahydropyranyl; for histidine:benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be glycinamide, a particularly useful support is the benzhydrylamino-polystyrene-divinylbenzene polymer described by P. Rivaille, et al, *Helv. Chim. Acta.*, 54, 2772 (1971). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Bocamino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichloromethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide (DIC) or other carbodiimide either alone or in the presence of HBT, N-hydroxysuccinimide, other N-hydroxyimides or oximes. Alternatively, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine of fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by silica gel chromatography. The removal of the side chain protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about $-10°$ and $+10°$ C., preferably about 0° C., for between about 15 minutes and 1 hour, preferably about 30 minutes. For the glycine terminal peptides on the benzyhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing.

If a racemic amino acid is used in the 1, 2, 3 or 6 position, the diastereomeric nonapeptide or decapeptide final products are separated, and the desired peptide containing a D-amino acid in the appropriate position is isolated and purified, preferably during the above-described chromatographic process.

The preparation of peptides having C-terminal azaglycine amides is preferably done using classical peptide solution synthesis using known peptide intermediates.

The compounds of formula II may be prepared by two methods. One method follows classic peptide synthesis techniques. An ω-amino-α-amino acid is treated with appropriate protecting groups in such a way that the acid function and the α-amino group are protected but leaving the ω-amino function available for further treatment. This protected compound is then reacted with N,N'-dialkylcarbodiimide in an appropriate solvent. The reaction is carried out at temperature between about 22°–150° C. for up to about 6 hours. The solvent is then removed. In order to remove the N,N'-dialkylurea by-product, the residue is suspended in a second solvent such as dimethylformamide and the suspension filtered to recover the desired product as a solid. Alternatively, the corresponding N,N'halodialkylthiourea may be reacted with the ω-function of a suitably protected amino acid (eg. CBZ-Lys-OBZl) in the presence of $HgCl_2$.

Alternatively, lysine dihydrochloride or appropriate homolog is reacted with an S-methyl-dialkyl-isothiourea.HI or the corresponding free base in the presence of a solution of a strong base such as sodium hydroxide, potassium hydroxide or the like. The reaction is best effected at from room temperature to 90° C., preferably 60° C. over several days, i.e., 2–6 days at a pH of ca. 10.5. Additional thiourea may be added if needed after the initial reaction period. A dialkyl dicarbonate and base such as magnesium oxide is then added in an organic solvent, such as dioxane, to react with the α-amino function of the product and the α, ω-functions of excess starting material. The reaction product is then worked up by extraction, an ion exchange resin treatment and other appropriate chromatographic means. The following examples illustrate the preparation of compounds within the scope of this invention.

PREPARATION 1

A mixture of 17.5 g $NaHCO_3$, 125 ml methylene chloride and 2.65 ml thiophosgene was cooled to 0° C.

and a solution of 9.4 g of $CF_3CH_2NH_2.HCl$ in 50 ml of water was added dropwise. The reaction mixture was stored at 0° for 2 hr. and then at room temperature overnight.

The mixture was partitioned between methylene chloride and water. The methylene chloride layer was drie over magnesuim sulfate. The methylene chloride solution was filtered and concentrated to an oil. The oil was crystallized from ethyl acetate/hexane to yield 6.5 g of N,N'-bis-(2,2,2-trifluoroethyl)urea of mp. 154°–5° C.

A solution of 3.36 g of the above urea in 10 ml of methanol was treated with 0.96 ml of $CH_3I$. The reaction mixture was heated at 70° C. for 1 hr. An additional 0.96 ml of $CH_3I$ was added and stirring was continued for 2 hr. at 70° C., then overnight at room temperature.

The solvent was evaporated in vacuo and the residue was crystallized from MeOH/diethyl ether to yield S-methyl N,N'-bis-(2,2,2-trifluoroethyl)-iso-thiouronium iodide of mp 145°–6° C., In a similar fashion substituting:
2,2,2-trichloropropylamine,
trifluoromethylamine,
2,2,3,3,3-pentafluoropropylamine
and the like there are obtained:
S-methyl N,N'-bis(2,2,2-trichloropropyl)-iso-thioruonium iodide,
S-methyl N,N'-bis(trifluoromethyl)-iso-thiouronium iodide, and
S-methyl N,N'-bis(2,2,3,3,3-pentafluoropropyl)-iso-thiouronium iodide

PREPARATION 2

A mixture of 5.42 g of benzyl $N^\alpha$-benzyloxycarbonyl-D-lysinate toluenesulfonate (B. Bezas and L. Zervas, *J. Am. Chem. Soc.*, 83, 719 (1961)) and diisopropylethylamine 1.72 ml of in 60 ml of dioxane is created with 3.6 g of S-methyl-N,N'-bis(2,2,2-trifluoroethyl)-isothiourea. The reaction mixture is stirred at 100° C. for 6 hours, cooled to room temperature and concentrated to a solid. The solid is suspended in 20 ml of warm DMF, filtered and the filtrate concentrated to a solid. Benzyl $N^\alpha$-benzyloxycarbonyl-N,N'-guanidino-bis(2,2,2-trifluoroethyl)-D-homoargininate toluenesulfonate is obtained as a white solid by crystallization from methanol/ethyl acetate.

Similarly, by using the above procedure, but substituting:
N,N'-bis(2,2,2-trichloropropyl)carbodiimide;
N,N'-bis(trifluoromethyl)carbodiimide;
N,N'-bis(2,2,3,3,3-pentafluoropropyl)carbodiimide;
and the like, there are obtained:
benzyl $N^\alpha$-benzyloxycarbonyl-N,N'-guanidino-bis(2,2,2-trichloropropyl)-D-homoargininate;
benzyl $N^\alpha$-benzyloxycarbonyl-N,N'-guanidino-bis(trifluoromethyl)-D-homoargininate; and
benzyl $N^\alpha$-benzyloxycarbonyl-N,N'-guanidino-bis(2,2,3,3,3-pentafluoropropyl)-D-homoargininate.

Similarly, by substituting benzyl $N^\alpha$-benzyloxycarbonyl-D-ornithinate for the D-lysinate there may be obtained the corresponding D-arginine analogs as their toluenesulfonate salts.

PREPARATION 3

A solution of 6 g of benzyl $N\alpha$-benzyloxycarbonyl-N,N'-guanidino-bis-(2,2,2-trifluoroethyl)-D-homoarginiate in 150 ml of ethanol containing 1 g of 10% Pd/C catalyst was treated with hydrogen gas for 3 hr at ambient pressure. An additional 0.4 g of 10% Pd/C was added and hydrogenolysis continued for an additional 3 hr.

The reaction mixture was filtered through Celite and concentrated to dryness to yield N,N'-guanidino-bis-(2,2,2-trifluoroethyl)-D-homoarginine as a white foam of $[\alpha]_D^{25} - 6.1°$ (C 0.6, MeOH).

A solution of 1.96 g of the above named free amino acid in a mixture of 8 ml 1N NaOH and 8M dioxane was treated with 1.05 g di-t-butyldicarbonate and 0.16 g MgO at 0° C. for 1 hr and for 3 at room temperature. The mixture was filtered, concentrated to dryness, diluted with water and washed with diethyl ether. The aqueous layer was acidified at 0° C. with 1N HCL to a pH of 3.5 and was then extracted with ethyl acetate. The ethyl acetate layer was washed with water, sat. NaCl, and dried over magnesium sulfate. The ethyl acetate extract was filtered and concentrated to give a white foam. The foam was triturated with $Ag_3$ (Cl$^-$) resin to give 1.4 g of N$\alpha$-t-butoxycarbonyl-N,N'-guanidino-bis-(2,2,2-trifluoroethyl)-D-homoarginine hydrochloride of mp 122°–130° C., $[\alpha]_D^{25} - 2.2°$ (CO.5, MeOH).

In a similar fashion, substituting the products of Preparation 2 were obtained the corresponding Boc protected homoarginine and arginine derivatives.

PREPARATION 4

Cis-5-alkylproline compounds may be prepared by the following method:

To a 200-ml round-bottomed flask is added (S)-3-(benzyloxycarbonyl)-5-oxo-4-oxazolidinepropionic acid and 63 ml of anhydrous benzene. To this solution is added 13.9 g of phosphorus pentachloride at 0° C. The reaction mixture is stirred at 0° C. for 1 hr during which time all of the phosphorus pentachloride dissolves. The benzene solvent is removed under vacuum and coevaporation with two 25 ml samples of dry benzene, and the residue dried under vacuum to give a light solid. The light solid is suspended in 30 ml of hexamethylphosphoramide and 9.4 ml of tetramethyltin and 40 mg of $PhCH_2Pd(PPh_3)_2Cl$ is added. The reaction mixture is heated at 65° C. for 4 hours. An additional 2 ml of tetramethyltin is added at the end of that period and the reaction mixture is stirred over night at room temperature.) After dilution with water and extraction with ethyl acetate, the ethyl acetate layer is washed with water, 5% sodium bicarbonate, water, 5% sodium bisulfate, water, and saturated sodium chloride and dried over anhydrous magnesium sulfate. The solution is filtered and concentrated to give 16 g of a yellow oil, which is passed through a silica gel column using ethyl acetate/hexane(4/6) as eluent. Concentration of the appropriate fractions gives 15 g of a light yellow oil which is recrystallized from ethyl acetate-hexane to produce 14.3 g of (S)-3-(benzyloxycarbonyl)-4-(3-oxobutyl)-5-oxazolidinone as a white solid (74% yield), having a mp of 64°–65° C., $[\alpha]_D^{25} = +102°$ (c=1.1, $CH_2Cl_2$).

Anal: Calcd. for $C_{18}H_{17}NO_5$: C, 61.85; H, 5.84; N, 4.81. Found: C, 61.54; H, 5.89; N, 4.84.

By repeating the above procedure in a similar manner, and, by replacing the tetramethyltin with a stoichiometrically equivalent of the appropriate tetraalkyltin the following compounds are prepared:

13

(a) With tetraethyltin (S)-3-(Benzyloxycarbonyl)-4-(3-oxopentyl)-5-oxazolidinone having a mp of 45°–46° C.;
$[\alpha]_D^{25} = 82.5°$ (c 0.7, $CH_3OH$).

Anal: Calcd. for $C_{16}H_{19}NO_5$ (305.336): C, 62.94; H, 6.37; N, 4.59. Found: C, 63.02; H, 6.15; N, 4.48.

(b) With tetrabutyltin (S)-3-(Benzyloxycarbonyl)-4-(3-oxoheptyl)-5-oxazolidinone as an oil; $[\alpha]_D^{25}$ 67.9° (c 0.12, $CH_3OH$).

Anal: Calcd. for $C_{18}H_{23}NO_5$·EtOAc (421.494): C, 62.69; H, 7.41; N, 3.32. Found: C, 62.50; H, 7.29; N, 3.39.

Ten grams of the (S)-3-(benzyloxycarbonyl)-4-(3-oxobutyl)-5-oxazolidinone from Example 4 is dissolved in 480 ml of distilled tetrahydrofuran, followed by 160 ml of ammonia at 0° C. The reaction mixture is stirred at 0° for 5 hours, then at ambient temperature overnight. After stripping under vacuum to dryness, the reaction mixture yields a white solid which is recrystallized from hot ethyl acetate to give 8.8 g of (S)-2-(benzyloxycarbonylamino)-5-oxo-hexanamide as a white solid (82% yield), mp 142°–144°; $[\alpha]_D^{25} = -4.0°$ (c 0.4, $CH_3OH$).

Anal.: Calcd. for $C_7H_9NO_2$: C, 60.4; H, 6.4; N, 10.0. Found: C, 60.44; H, 6.53; N, 10.05.

By repeating the above procedure in a similar manner and substituting a stoichiometrically equivalent of the corresponding intermediates from the second previous paragraph, the following compounds are prepared:

(S)-2-Benzyloxycarbonylamino-5-oxo-heptanamide having a mp of 133°–135° C.; $[\alpha]_D^{25}$ −4.17° (c 0.8, $CH_3OH$).

Anal: Calcd. for $C_{15}H_{20}N_2O_4$ (292.341): C, 61.63; H, 6.90; N, 9.58. Found: C, 61.51; H, 6.75; N, 9.16.

(S)-2-Benzyloxycarbonylamino-5-oxo-nonamide having a mp of 162°–163° C.; $[\alpha]_D^{25}$ −4.32° (c 0.6, $CH_3OH$).

Anal: Calcd. for $C_{17}H_{24}N_2O_4$ (320.395): C, 63.73; H, 7.55; N, 8.74. C, 63.62; H, 7.56; N, 8.82.

To a solution of 2.8 g of (S)-2-benzyloxycarbonylamino)-5-oxohexanamide from the preceding paragraph in a mixture of 60 ml of methanol and 7.5 ml of glacial acetic acid is added, under nitrogen, 1.5 g of palladium diacetate. This reaction mixture is hydrogenated under atmospheric pressure for 4 hrs, at which time a thin layer chromagraphic analysis shows the reaction had gone to completion. The reaction mixture is then filtered through Celite and washed with methanol. The reaction mixture and washings are concentrated to dryness to give 1.7 g of a yellow oil, which is treated with 1 ml of a mixture of hydrochloric acid and ethyl acetate to produce the hydrochloride salt. This oil is triturated with methanol/ethyl ether to produce 1.3 g of a yellow solid; mp 174°–176° C.; $[\alpha]_D^{25} = -33°$ (c 0.96, $CH_3OH$). The yellow solid of (S)-cis-5-methylprolinamide (as the hydrochloride salt) is passed through a Bio-Rex 70 column (a weakly acid carboxylic acid ion-exchange resin) with elution first with 300-ml of water, followed by 1% solution of ammonium hydroxide. Concentration of the appropriate fractions gives a 0.9 g of a yellow solid, which is recrystallized from methylene chloride to produce 0.64 g of (S)-cis-S-methylprolinamide as a yellow solid (50% yield); mp 55°–56° C.

By repeating the above procedure in a similar fashion, and substituting a stoichiometrically equivalent of the corresponding intermediate, the following compounds are prepared after reduction:

14

(S)-cis-5-ethylprolinamide, mp 63°–65° C.; and
(S)-cis-5-butylprolinamide, mp 74°–75° C.

PREPARATION 5

4.9 g of Boc-glycine was dissolved in a mixture of 50 ml. ethanol and 50 ml. distilled water. The pH of the solution was brought to 7 with aqueous cesium bicarbonate. The solvent was then removed under vacuum. After 18 hours of drying under high vacuum, the residue was dissolved in 150 ml. dry DMF. 25 g chloromethylated polystyrene—1% divinylbenzene (Merrifield) resin (corresponding to 25 mmole chloride) was added. The mixture was shaken at 50° C. for 24 hours, filtered, and the resin was then washed sequentially with DMF, water, and ethanol. The resin was dried under vacuum for 3 days to yield 28.34 g of Boc-Gly-O-Resin.

EXAMPLE 1

In the reaction vessel of a Beckman 990 Peptide Synthesizer was placed 0.5 g (0.5 mmol.) of benzhydrylamine resin (Beckman). Amino acids were added sequentially to this resin by means of a synthesis program, as follows:

| Step | | | |
|---|---|---|---|
| 1 | $CH_2Cl_2$ wash | 1 time | 1.5 min |
| 2 | 50% $CF_3CO_2H/CH_2Cl_2$ - deprotection | 1 time | 1.5 min |
| 3 | 50% $CF_3CO_2H/CH_2Cl_2$ - deprotection | 1 time | 30 min |
| 4 | $CH_2Cl_2$ wash | 3 times | 1.5 min |
| 5 | 10% triethylamine/$CH_2Cl_2$ | 2 times | 1.5 min |
| 6 | $CH_2Cl_2$ wash | 3 times | 1.5 min |
| 7 | $N^\alpha$—Boc-amino acid solution | 1 time | add |
| 8 | N,N'—dicyclohexylcarbodiimide solution | 1 time | add |
| 9 | $CH_2Cl_2$ rinse and hold - coupling | 1 time | coupling reaction 2 hr |
| 10 | $CH_2Cl_2$ -rinse add | 1 time | 1.5 min |
| 11 | $CH_2Cl_2$ wash | 3 times | 1.5 min |
| 12 | ethanol wash | 3 times | 1.5 min |
| 13 | $CH_2Cl_2$ wash | 3 times | 1.5 min |

Steps 1–13 complete a coupling cycle for one amino acid and completeness of the reaction is checked by the ninhydrin method of E. Kaiser, et al., *Anal. Biochem.*, 34, 595 (1970).

The resin was coupled sequentially with a 2.0 to 2.5 molar excess of each protected amino acid and DCC with or without additions such as 1-hydroxybenzotriazol (HBT). Thus, the resin was treated during successive coupling cycles with 0.237 g of Boc-D-AlaOH and 0.155 g of BHT 0.269 g. Boc-Pro-OH,
0.536 g. Boc-Arg(Tosyl)-OH,
0.312 g. Boc-Leu-OH.$H_2O$
0.488 g. Boc-D-FDeh-OH.HCl and 0.155 g BHT,
0.44 g. Boc-Tyr(2,6-dichlorobenzyl)-OH and 0.155 g BHT,
0.375 g. Boc-Ser(Benzyl)-OH,
0.380 g. Boc-D-Trp-OH,
0.375 g. Boc-D-p-Cl-Phe-OH and 0.155 g BHT,
0.275 g. Boc-D-Nal(2)-OH and 0.155 g BHT, and
2.0 ml. acetic anhydride.

The resin was removed from the reaction vessel, washed with $CH_2Cl_2$, and dried in vacuo to yield 1.64 g. of protected polypeptide resin. The protected peptide was removed from the resin and deprotected by treatment with 25 ml. anhydrous liquid HF in the presence of 3.2 ml. of anisole (scavenger) in a Kel-F reaction vessel at 0° C. for 1 hour. The HF was evaporated under vacuum and the residue of N-Ac-D-Nal(2)-D-p-Cl-Phe-D-Trp-Ser-Tyr-D-FDeh-Leu-Arg-Pro-D-AlaNH$_2$, as its HF salt, was washed with ether. The residue was then extracted with glacial acetic acid. The acetic acid extract was lyophilized to yield the crude material.

The crude material was converted to the acetate salt by passage in water through a column of AG3X (a weakly basic tertiary amine resin) which had been converted to the acetate form. Lyophilization of the eluate yielded 0.6 g. of the crude peptide acetate salt as a white solid.

The crude peptide was purified by high performance liquid chromatography on a 2.5×100 cm. column of Licroprep Rp-18 (25–40 micron) equilibrated to the running buffer 55% CH$_3$CN/45% H$_2$O (0.06M in NH$_4$OAc, pH 7). The major UV absorbing (280 nm) peak eluting at approximately 4 column volumes was collected, concentrated to dryness, and lyophilized 3 times from distilled water to yield 124 mg of pure N-Ac-D-Nal(2)-D-p-Cl-Phe-D-Trp-Ser-Tyr-D-FDeh-Leu-Arg-Pro-D-AlaNH$_2$, $[\alpha]_D^{22} = -15.4°$ (C 0.5, HOAc).

Proceeding in a similar manner but substituting the appropriate A, B, C, D, E, G or F amino acid for those recited, there are prepared the corresponding D-AlaNH$_2$ decapeptides exemplified below.

EXAMPLE 2

For the synthesis of analogues with a C-terminal Pro-NHCH$_2$CH$_3$, a synthesis program identical to that described in Example 1 was used. The Beckman 990 Synthesizer reaction vessel was loaded with 2.13 g. of Boc-Pro-O-Resin, prepared by the reaction of equimolar ratios of the dry cesium salt of Boc-Pro-OH with chloromethyl-polystyrene/1% divinylbenzene (Lab Systems, Inc.). The quantity of Boc-Pro-O-Resin taken contained 1.4 mmol. of proline.

The resin was coupled sequentially with a 2.0 to 2.5 molar excess of each protected amino acid and DCC. Thus, the resin was reacted during successive coupling cycles with
1.49 g. Boc-Arg(Tosyl)-OH,
0.87 g. Boc-Leu-OH H$_2$O,
1.34 g. Boc-N,N'-guanido-bis(2,2,2-trifluoroethyl-D-homoarginine,
0.38 g. 1-hydroxybenzotriazole,
1.23 g. N-Boc-O-2,6-dichlorobenzylbromobenzyloxycarbonyl-L-tyrosine and 0.38 g HBT,
1.03 g. Boc-Ser(Benzyl)-OH,
1.07 g. Boc-D-Trp-OH,
1.05 g. Boc-D-p-Cl-Phe-OH
1.10 g. Boc-D-Nal(2)-OH and
2 ml of acetic anhydride.

The resin was removed from the reaction vessel, washed with CH$_2$Cl$_2$, and dried in vacuo to yield the protected polypeptide resin.

The protected polypeptide was cleaved from the resin by aminolysis with 50 mL. of ethylamine for 18 hours at 2° C. The ethylamine was allowed to evaporate and the resin was extracted with methanol. The methanol was evaporated to yield the protected peptide ethylamide with 3 ml of anisole and 30 mL. redistilled (from CoF$_3$) anhydrous liquid HF at 0° C. for 30 minutes in a Kel-F reaction vessel. The HF was evaporated under vacuum and the residue was washed with ether. The residue was dissolved in 2M acetic acid and lyophilized to yield 0.82 g. of crude N-Ac-Nal(2)-D-p-Cl-Phe-D-Trp-Ser-Tyr-D-FDeh-Leu-Arg-Pro-NHEt as its acetic acid addition salt.

Final purification was achieved by preparative high performance liquid crhomatography of a 20 mg. sample on a 2.5×100 mm. column of 40–50 microns. octadecylsilylated silica (Merck, Lichroprep C$_{18}$) using 55%CH$_3$CN/45% H$_2$O eluent which was 0.06M in NH$_4$OAc (pH 7).

EXAMPLE 3

A. A solution of 0.1 g of the hydrogen fluoride N-Ac-D-Nal(2)-D-p-Cl-Phe-D-Trp-Ser-Tyr-D-FDeh-Leu-Arg-Pro-D-AlaNH$_2$, (See Example 1) is dissolved in 50 ml of water and passed through a column of 50 g Dowex 3 anion exchange resin which had previously been equilibrated with acetic acid and washed with deionized water. The column is eluted with deionized water and the effluent is lyophilized to yield the corresponding acetic.

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of the other peptides analogous to LHRH, described herein.

B. In the case of salts of lower water solubility, these may be prepared by precipitation from water utilizing the desired acid. For example:

Zinc tannate salt—a solution of 10 mg of N-Ac-D-Nal(2)-D-p-Cl-Phe-D-Trp-Ser-Tyr-D-FDeh-Leu-Arg-Pro-D-AlaNH$_2$ acetic acid salt in 0.1 mL of water was treated with a solution of 8 mg of tannic acid in 0.08 mL of 0.25M NaOH. A solution of 5 mg of ZnSO$_4$ heptahydrate in 0.1 mL of water was immediately added to the solution of the LHRH analogue.

The resultant suspension was diluted with 1 mL water and the precipitate was centrifuged. The supernatant was decanted and the residue was washed twice with 1 mL portions of water by centrifugation of the precipitate and decantation of the supernatant. The precipitate was dried in vacuo to yield 15 mg of the mixed zinc tannate salt of the above named LHRH analogue.

EXAMPLE 4

A solution of 10 mg of N-Ac-D-Nal(2)-D-p-Cl-Phe-D-Trp-Ser-Tyr-D-FDeh-Leu-Arg-Pro-D-AlaNH$_2$ 25 ml. of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid addition salts of compounds of the peptides herein may be converted to the corresponding free bases.

What is claimed is:

1. A compound of the formula

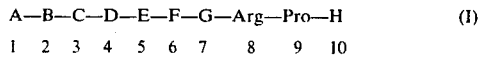  (I)

or a pharmaceutically acceptable salt thereof, wherein:
A is an amino acyl residue selected from the group consisting of N-Ac-D,L-Δ$^{3,4}$-prolyl, N-Ac-D,L-prolyl, N-Ac-L-alkylprolyl, N-Ac-D,L-phenylalanyl, N-Ac-D,L-p-Cl-phenylalanyl, N-Ac-D,L-seryl, N-Ac-D,L-threonyl, N-Ac-D,L-alanyl, N-Ac-3-(1-naphthyl)-D,L-alanyl, N-Ac-3-(2-naphthyl)-D,L-alanyl, N-Ac-3-(2,4,6-trimethylphenyl)-D,L-alanyl, and N-Ac-3-(4-trifluoromethylphenyl)-D,L-alanyl;

B is an amino acyl residue selected from the group consisting of D-phenylalanyl, D-p-Cl-phenylalanyl, D-p-Br-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanyl and 3-(2,4,6-trimethylphenyl)-D-alanyl;

C is an amino acyl residue selected from the group consisting of D-tryptophanyl, D-phenylalanyl, D-pentamethyl-phenylalanyl, 3-(3-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl residue selected from the group consisting of the radicals represented by the following structural formula:

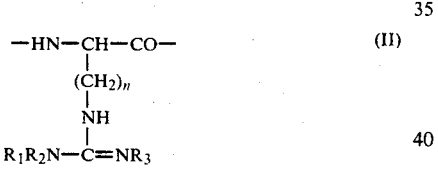  (II)

wherein
n is 1 to 5;
R$_1$ is lower alkyl substituted with one to three halo atoms;
R$_2$ is hydrogen;
R$_3$ is R$_1$, methyl, ethyl or —CH$_2$CH$_2$OH;
G is an amino acyl residue selected from the group consisting of L-leucyl, L-norleucyl, L-tryptophanyl, L-Nal(2) and L-norvalyl; and
H is D-alaninamide, D-leucinamide, glycinamide or —NHR$_5$ wherein R$_5$ is lower alkyl or NHCONH$_2$.

2. The compound of claim 1 wherein n is 3 or 4.

3. The compound of claim 2 which is N-Ac-D-Nal(2)-D-p-Cl-Phe-D-Trp-Ser-Tyr-D-FDeh-Leu-Arg-Pro-D-AlaNH$_2$ or a pharmaceutically acceptable salt thereof.

4. The compound of claim 2 which is N-Ac-D-Nal(2)-D-p-Cl-Phe-D-Trp-Ser-Tyr-D-FDeh-Trp-Arg-Pro-D-AlaNH$_2$ or a pharmaceutically acceptable salt thereof.

5. The compound of claim 2 which is N-Ac-D-Nal(2)-D-p-Cl-Phe-D-Trp-Ser-Tyr-D-FDeh-Nal(2)-Arg-Pro-D-AlaNH$_2$ or a pharmaceutically acceptable salt thereof.

6. The compound of claim 2 which is N-Ac-D-Nal(2)-D-p-Cl-Phe-D-Trp-Ser-Tyr-D-mfph-Nal(2)-Arg-Pro-D-AlaNH$_2$ or a pharmaceutically acceptable salt thereof.

7. A compound of the formula

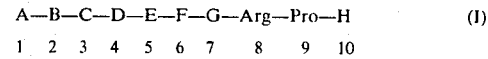  (I)

or a pharmaceutically acceptable salt thereof, wherein:
A is an amino acyl residue selected from the group consisting of N-Ac-D,L-Δ$^{3,4}$-prolyl, N-Ac-D,L-prolyl, N-Ac-L-alkylprolyl, N-Ac-D,L-phenylalanyl, N-Ac-D,L-p-Cl-phenylalanyl, N-Ac-D,L-seryl, N-Ac-D,L-threonyl, N-Ac-D,L-alanyl, N-Ac-3-(1-naphthyl)-D,L-alanyl, N-Ac-3-(2-naphthyl)-D,L-alanyl, N-Ac-3-(2,4,6-trimethylphenyl)-D,L-alanyl, and N-Ac-3-(4-trifluoromethylphenyl)-D,L-alanyl;

B is an amino acyl residue selected from the group consisting of D-phenylalanyl, D-p-Cl-phenylalanyl, D-p-Br-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanyl and 3-(2,4,6-trimethylphenyl)-D-alanyl;

C is an amino acyl residue selected from the group consisting of D-tryptophanyl, D-phenylalanyl, D-pentamethyl-phenylalanyl, 3-(3-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl residue selected from the group consisting of the radicals represented by the following structural formula:

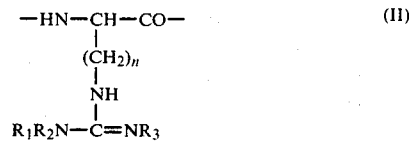  (II)

wherein
n is 1 to 5;
R$_1$ is lower alkyl substituted with one to three fluoro atoms;
R$_2$ is hydrogen;
R$_3$ is R$_1$, methyl, ethyl or —CH$_2$CH$_2$OH;
G is an amino acyl residue selected from the group consisting of L-leucyl, L-norleucyl, L-tryptophanyl, L-Nal(2) and L-norvalyl; and
H is D-alaninamide, D-leucinamide, glycinamide or —NHR$_5$ wherein R$_5$ is lower alkyl or NHCONH$_2$.

8. A compound of claim 7 wherein the one to three fluoro atoms substituted on the lower alkyl group of R$_1$ are on the ω-carbon of said lower alkyl group.

9. A compound of the formula

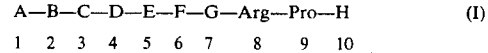  (I)

or a pharmaceutically acceptable salt thereof, wherein:
A is an amino acyl residue selected from the group consisting of N-Ac-D,L-Δ$^{3,4}$-prolyl, N-Ac-D,L-prolyl, N-Ac-L-alkylprolyl, N-Ac-D,L-phenylalanyl, N-Ac-D,L-p-Cl-phenylalanyl, N-Ac-D,L-seryl, N-Ac-D,L-threonyl, N-Ac-D,L-alanyl, N-Ac-3-(1-naphthyl)-D,L-alanyl, N-Ac-3-(2-naphthyl)-D,L-alanyl, N-Ac-3-(2,4,6-trimethylphenyl)-D,L-alanyl, and N-Ac-3-(4-trifluoromethylphenyl)-D,L-alanyl;

B is an amino acyl residue selected from the group consisting of D-phenylalanyl, D-p-Cl-phenylalanyl, D-p-Br-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanyl and 3-(2,4,6-trimethylphenyl)-D-alanyl;

C is an amino acyl residue selected from the group consisting of D-tryptophanyl, D-phenylalanyl, D-pentamethyl-phenylalanyl, 3-(3-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl residue selected from the group consisting of the radicals represented by the following structural formula:

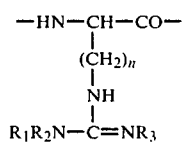

wherein
n is 1 to 5;
$R_1$ is trifluoroethyl;
$R_2$ is hydrogen;
$R_3$ is trifluoroethyl;
G is an amino acyl residue selected from the group consisting of L-leucyl, L-norleucyl, L-tryptophanyl, L-Nal(2) and L-norvalyl; and
H is D-alaninamide, D-leucinamide, glycinamide or —$NHR_5$ wherein $R_5$ is lower alkyl or $NHCONH_2$.

10. A compound of claim 9 wherein the three fluoro atoms substituted on the ethyl group of $R_1$ are on the ω-carbon of said ethyl group.

11. A pharmaceutical composition for use as a LHRH antagonist comprising a therapeutically effective amount of a compound of claim 1 in admixture with at least one pharmaceutically acceptable excipient.

12. A method for treating endometriosis in a female subject, said method comprising administering to said subject, a therapeutically effective amount of a compound of claim 1.

13. A method for treating endometriosis in a female subject, said method comprising administering to said subject, a therapeutically effective amount of a compound of claim 3.

* * * * *